United States Patent [19]

Heywang et al.

[11] Patent Number: 5,473,079
[45] Date of Patent: Dec. 5, 1995

[54] PROCESS FOR PREPARING 2-ARYLBENZIMIDAZOLE-5-SULFONIC ACIDS

[75] Inventors: Ulrich Heywang, Darmstadt; Ingeborg Stein, Erzhausen; Ulrich Fechtel, Ober-Ramstadt; Michael Casutt, Heppenheim; Gerald Faller, Bensheim; Hartmut Härtner, Mühlta, all of Germany

[73] Assignee: Merck Patent Gesellschaft Mit Beschrankter Haftung, Darmstadt, Germany

[21] Appl. No.: 122,566
[22] PCT Filed: Jan. 27, 1993
[86] PCT No.: PCT/EP93/00179
§ 371 Date: Sep. 30, 1993
§ 102(e) Date: Sep. 30, 1993
[87] PCT Pub. No.: WO93/15061
PCT Pub. Date: Aug. 5, 1993

[30] Foreign Application Priority Data

Feb. 4, 1992 [DE] Germany .................. 42 03 072.2

[51] Int. Cl.[6] ................ C07D 235/18; A61K 31/415
[52] U.S. Cl. ................ 548/305.4; 548/307.1; 548/310.1; 548/316.1
[58] Field of Search .............. 548/305.4, 310.1, 548/310.7, 307.1

[56] References Cited

U.S. PATENT DOCUMENTS

| | | | |
|---|---|---|---|
| 2,463,264 | 3/1949 | Graenacher et al. | 548/305.4 |
| 3,324,050 | 6/1967 | Joo et al. | 548/305.4 X |
| 3,536,730 | 10/1970 | Baron et al. | 548/305.4 |
| 3,586,673 | 6/1971 | Bloom et al. | 548/305.4 X |
| 3,655,632 | 4/1972 | Ohfuji et al. | 548/305.4 X |
| 4,263,441 | 4/1981 | Pintschovius et al. | 548/305.4 X |
| 4,309,551 | 1/1982 | Schönberger et al. | 548/305.4 X |
| 4,585,875 | 4/1986 | Heiss | 548/156 |

FOREIGN PATENT DOCUMENTS

| | | | |
|---|---|---|---|
| 0470661 | 1/1951 | Canada | 548/305.4 |
| 1450505 | 8/1966 | France | 548/305.4 |
| 0445957 | 2/1950 | Italy | 548/305.4 |
| 1124558 | 8/1968 | United Kingdom | 548/305.4 |

OTHER PUBLICATIONS

K. K. Preobrazhenskii, et al., "2–Alkylbenzimidazoles and their sulfo derivatives", *Chemical Abstracts*, vol. 84, No. 7, Abstract No. 30963t (Aug. 14, 1976), p. 454.

L. S. Efros, "Imidazole derivatives. VII. Preparation of sulfonic acids of benzimidazole by baking method", *Chemical Abstracts*, vol. 48, see Column 4524, (1953).

Primary Examiner—Floyd D. Higel
Attorney, Agent, or Firm—Millen, White, Zelano, & Branigan

[57] ABSTRACT

The invention relates to an improved process for preparing 2-arylbenzimidazole-5-sulfonic acids of the formula I,

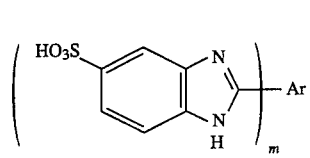

in which
Ar is unsubstituted phenyl or phenyl substituted by one or more $C_1$–$C_6$ alkyl or alkoxy groups and
m is 1, 2 or 3,
wherein o-phenylenediamine is reacted in the presence of sulfuric acid at between room temperature and 250° C. with a benzoic acid derivative of the formula II $$Ar(-X)_m \qquad\qquad II$$

in which Ar and m are as above, and X is COO-alkyl, where alkyl is n-alkyl having from 1 to 6 C atoms, COOH, COCl, COBr or CN, and new arylbenzimidazole acids of the formula Ia

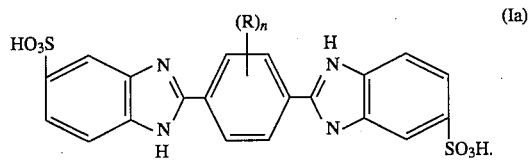

8 Claims, No Drawings

PROCESS FOR PREPARING 2-ARYLBENZIMIDAZOLE-5-SULFONIC ACIDS

This application is a 371 of PCT/EP93/00179 filed Aug. 27, 1993.

The invention relates to an improved process for preparing 2-arylbenzimidazole-5-sulfonic acids of the formula I,

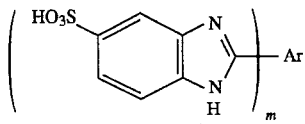

in which

Ar is unsubstituted phenyl or phenyl substituted by one or more $C_1$–$C_6$ alkyl or alkoxy groups and m is 1, 2 or 3, wherein o-phenylenediamine is reacted in the presence of sulfuric acid at between room temperature and 250° C. with a benzoic acid derivative of the formula II

   II in which Ar and m are as above, and X is COO-alkyl, where alkyl is n-alkyl having from 1 to 6 C atoms, COOH, COCl, COBr or CN.

2-Phenylbenzimidazole-5-sulfonic acid (Eusolex 232) is an important water-soluble UV-B radiation filter with wide application in cosmetics. Its use as a UV radiation filter is described, for example, in German Reich Patent No. 676 103.

Its preparation proceeds, according to, for example, V. G. Sayapin et al., KhGC [Chemistry of Heterocyclic Compounds] 6, 1970, 630–632, in a two-stage reaction in which 2-phenylbenzimidazole is first prepared from 1,2-phenylenediamine and the bisulfite adduct of benzaldehyde or from phenylenediamine and benzoic acid in the presence of polyphosphoric acid, and is then reacted with chlorosulfonic acid. A survey of the preparation of 2-substituted benzimidazoles can be found, for example, in Chemical Reviews Vol. 74, No. 3, 1974 p 279 ff.

This process nevertheless has great disadvantages:

a) It is a two-stage process and therefore more complicated and more expensive.

b) Industrial handling of chlorosulfonic acid causes problems since 2-phenylbenzimidazole disulfonic acids can be formed which can be separated out only with difficulty.

c) In the first preparation processes for phenylbenzimidazole, sodium hydrogen sulfite must be used in large excess, so that large amounts of sulfur dioxide are given off during working up; 1-benzyl-2-phenylbenzimidazole can be formed as a byproduct, which can be separated out only with difficulty. In the second process for preparing phenylbenzimidazole from benzoic acid phosphoric acid passes into the waste water, which is undesirable because Of eutrophication of water courses and lakes.

The disadvantages of the abovementioned process can be conveniently circumvented: it has surprisingly been found that in the condensation reaction of 1,2-diphenylenediamine with benzoic acid in sulfuric acid at high temperatures intermediate products are directly sulfonated, so that 2-phenylbenzimidazole-5-sulfonic acid is formed directly without isolation of an intermediate.

DE 12 82 855 describes the use of 1,3-bis-(5-sulfobenzimidazol-2-yl)benzene as a water-soluble UV-B radiation filter.

Its preparation proceeds analogously to that of 2-phenylbenzimidazole in a two-stage process.

The invention thus relates to an improved process for preparing 2-arylbenzimidazole-5-sulfonic acids of the formula I,

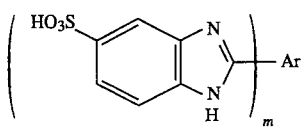

in which

Ar is unsubstituted phenyl or phenyl substituted by one or more $C_1$–$C_6$ alkyl or alkoxy groups and m is 1, 2 or 3, wherein o-phenylenediamine is reacted in the presence of sulfuric acid at between room temperature and 250° C. with a benzoic acid derivative of the formula II

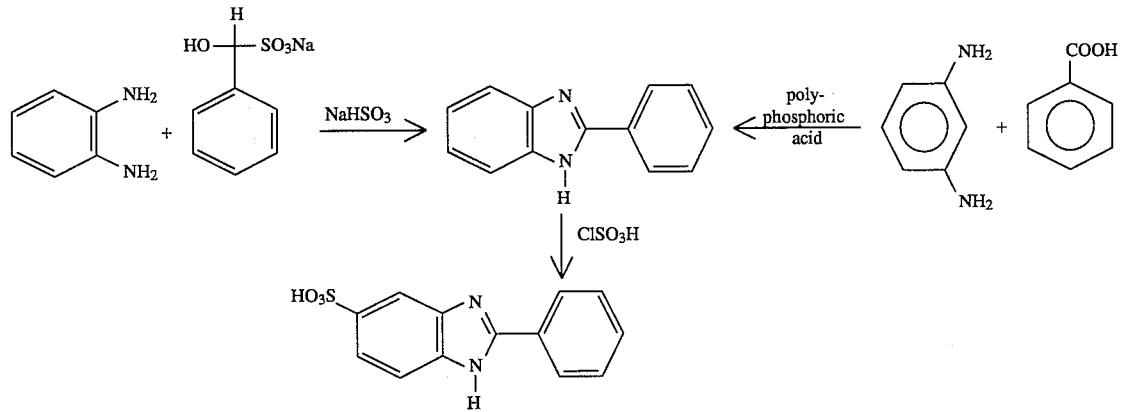

Ar(—X)$_m$   II in which Ar and m are as above, and X is COO-alkyl, where alkyl is n-alkyl having from 1 to 6 C atoms, COOH, COCl, COBr or CN, in particular where from 1 to 10 mol, preferably from 3 to 8 mol, particularly from 4 to 7 mol of sulfuric acid are used per 1 mol of o-phenylenediamine.

The invention further relates to such a process in which the benzoic acid derivative is introduced into the sulfuric acid, o-phenylenediamine of the formula II is subsequently added, and the mixture is heated to from 150° C. to 220° C., or in which o-phenylenediamine and the benzoic acid derivative are introduced together into the sulfuric acid.

A further preferred embodiment is a process in which the sulfuric acid is used as solvent, particularly in which 50–100% sulfuric acid is used and/or in which the solvent contains from 1 to 50% of water.

In a particularly preferred embodiment of the process of the invention, the mixture of the reactants is stirred for about from 1 to 5 hours at temperatures between 80° and 140° C., subsequently heated to temperatures between 170° and 250° C. and stirred for another 0.5 to 5 hours.

Carrying out the process of the invention per se is simple. The sulfuric acid, preferably in the form of a 50–100% solution, in particular as a concentrated about 96% solution, forms the initial charge. In general from 1 to 10 mol, preferably from 3 to 8 mol, in particular from 4 to 7 mol of sulfuric acid are used per 1 mol of phenylenediamine.

The method of adding the reactants benzoic acid and phenylenediamine is not critical. In general one of the two reactants is added at room temperature, which generally causes the mixture to warm to temperatures between 80° and 140° C. The second reactant is slowly added at this temperature, during which the temperature of the reaction mixture may rise further.

The reaction mixture is subsequently heated slowly to temperatures between 165° and 250° C., preferably between 175° and 200°C., in particular to the boiling point of the mixture, and maintained at this temperature for from 1 to 5 hours, optionally with stirring. The reaction mixture is subsequently allowed to cool, preferably to temperatures between 100° and 150° C., and water is added.

After stirring for a short time, preferably from 20 minutes to 2 hours, at from 50° to 80° C., the solid components are separated off, preferably washed with warm water and dried.

Some of the compounds of the formula I are known and some are new. The invention relates also to the new compounds of the formula I, in particular the compounds of the formula Ia, in which m is 2 and Ar is a group of the formula

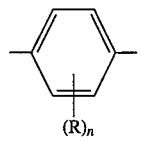

(R)$_n$ in which R is $C_{1-6}$-alkyl or alkoxy and n is 0, 1, 2, 3 or 4. Surprisingly, it has been found that the compounds of the formula Ia are suitable as water-soluble UV-A filters, whereas similar known compounds are UV-B filters.

To purify the dried crude product, the latter is preferably suspended in water and neutralized with diluted base. After purification of the solution so obtained, preferably with activated carbon, it is preferably heated to temperatures between 50° and 100° C. and acidified with a mineral acid, preferably concentrated hydrochloric acid. The precipitated sulfonic acid is separated off, washed with preferably warm water and dried.

In the formula I Ar is unsubstituted phenyl or phenyl substituted by one or more $C_1$–$C_6$ alkyl or alkoxy groups, preferably unsubstituted phenyl or phenyl substituted, particularly in the 4-, 3-, 3,4- or 3,5-position, by 1 or 2 $C_1$–$C_3$ alkyl or alkoxy groups, in particular unsubstituted phenyl. In the case where m=2 Ar is preferably 1-, 3- or 1,4-phenylene, in particular 1,4-phenylene. In the case where m=3 Ar is preferably benzene-1,3,5-triyl. In the formula II X is COO-alkyl, in which alkyl is n-alkyl having from 1 to 6 C atoms, preferably 1 or 2 C atoms, COOH, COCl or CN, preferably COOH, COOCH$_3$, COCl or CN, in particular COOH or CN.

The advantages of the process over the previously mentioned processes are:

a) Simple single-stage process, no difficulties with pH control.

b) The product is not contaminated by 1-benzyl-2-phenylbenzimidazole-6-sulfonic acid and 2-phenylbenzimidazoledisulfonic acids.

c) No elemental sulfur is formed, so that the waste water has a substantially lower chemical oxygen demand.

d) The intermediate products can be very simply and quickly centrifuged off and washed.

e) The yield is comparable to or greater than that in the processes known from the prior art.

f) Addition of sodium hydrogen sulfite is not needed, so that handling of sulfur dioxide is no longer necessary either.

The invention further relates to cosmetic preparations which contain an effective amount of at least one compound of the formula Ia in a carrier suitable for cosmetics.

Preference is given to such cosmetic preparations which contain from 0.1 to 10% by weight, preferably from 0.4 to 1.0% by weight, in particular about 0.5% by weight, of at least one compound of the formula Ia, in particular preparations which additionally contain a UV-B filter.

The invention further relates to the use of the compounds of the formula Ia as a cosmetic product or as a medicament.

The invention furthermore relates to the compound of the formula Ia for use in the preventive treatment of inflammations and allergies of the skin, and for use in the prevention of certain types of cancer.

The invention likewise relates to pharmaceutical preparations which contain an effective amount of at least one compound of the formula Ia in a physiologically tolerated carrier or excipient, in particular for topical application.

The invention furthermore relates to the use of the compounds of the formula Ia as medicaments.

Even without further explanations it is assumed that a person skilled in the art can use the above description in the widest scope. The preferred embodiments are hence to be taken as only descriptive, not as an in any way limiting disclosure.

The complete disclosure of all applications, patents and publications cited above or below, and the corresponding application P 42 03 072, filed on 04.02.92, granted on 03.07.92 as German Patent DE-42 03 072 C, is incorporated into this application by reference.

The examples below are intended to illustrate the invention.

Example 1

A 1 l three-necked flask is initially charged with 275 g (2.70 mol) of 96% sulfuric acid and subsequently 54.1 g (0.50 mol) of 1,2-phenylenediamine are carefully introduced. 85.5 g (0.70 mol) of benzoic acid are added to the suspension, which at this point has a temperature of about 120° C., and the mixture is heated while stirring (clear solution from about 130° C.) to about 200° C. for 5 hours, during which a small proportion of the benzoic acid sublimes. The mixture is then allowed to cool to about 150° C. and is stirred into 1 l of cold water, which warms to about 65° C. The mixture is stirred for a further hour at 65° C. and the precipitate is then filtered off with suction and washed with water at a temperature of 80° C. until free of sulfate. The dried crude product (83 g) is suspended in 830 ml of water and the pH is adjusted to 8 with 32% sodium hydroxide solution. After addition of 6.5 g of activated carbon the mixture is stirred for a further 30 minutes at room temperature and subsequently clarified by filtration. The filtrate is heated to 80° C. and the pH is adjusted to 3 with concentrated hydrochloric acid. The precipitated Eusolex 232 is filtered off with suction while warm, washed with 2 l of water at a temperature of 90° C. and dried to constant weight in a vacuum drying cabinet at 75° C. and 20 mbar. 67.0 g (245 mmol, 49% of theory) of 2-phenylbenzimidazole-5-sulfonic acid are obtained, 410° C. (decomposition).

The compounds below are prepared analogously:
2-(4'-methoxyphenyl)benzimidazole-5-sulfonic acid
2-(3'-methoxyphenyl)benzimidazole-5-sulfonic acid
2-(4'-ethoxyphenyl)benzimidazole-5-sulfonic acid  2-(3'-ethoxyphenyl)benzimidazole-5-sulfonic acid
2-(3',5'-dimethoxyphenyl)benzimidazole-5-sulfonic acid
2-(3',4'-dimethoxyphenyl)benzimidazole-5-sulfonic acid
2-(3',5'-diethoxyphenyl)benzimidazole-5-sulfonic acid
2-(3',4'-diethoxyphenyl)benzimidazole-5-sulfonic acid.

Example 2

The procedure is as in Example 1 but using 72.2 g (0.70 mol) of benzonitrile instead of benzoic acid. 72.0 g (263 mmol, 53% of theory) of 2-phenylbenzimidazole-5-sulfonic acid are obtained.

Example 3

The procedure is as in Example 1 but using 95.3 g (0.70 mol) of methyl benzoate instead of benzoic acid. 64.0 g (233 mmol, 47% of theory) of 2-phenylbenzimidazole-5-sulfonic acid are obtained.

Example 4

A 1 l three-necked flask is initially charged with 275 g (2.70 mol) of 96% sulfuric acid and subsequently 85.5 g (0.70 mol) of benzoic acid are introduced. 54.1 g (0.50 mol) of 1,2-phenyleneamine [sic] are carefully added, during which the mixture warms to about 100° C.; the mixture is then heated while stirring (clear solution from about 130° C.) to about 180° C. for 2 hours, during which a small proportion of the benzoic acid sublimes. The mixture is then stirred into 1 l of cold water, which warms to about 65° C. The mixture is stirred for a further hour at 65° C. and the precipitate is then filtered off with suction and washed with water at a temperature of 80° C. until free of sulfate. The dried crude product (83 g) is suspended in 830 ml of water and the pH is adjusted to 8 with 32% sodium hydroxide solution. After addition of 6.5 g of activated carbon the mixture is stirred for a further 30 minutes at room temperature and subsequently clarified by filtration. The filtrate is heated to 80° C. and the pH is adjusted to 3 with concentrated hydrochloric acid. The precipitated Eusolex 232 is filtered off with suction while warm, washed with 2 l of water at a temperature of 90° C. and dried to constant weight in a vacuum drying cabinet at 75° C. and 20 mbar. 67.0 g (245 mmol, 49% of theory) of 2-phenylbenzimidazole-5-sulfonic acid are thus obtained.

Example 5

A 2 l four-necked flask is initially charged with 182 ml of distilled water, and 1533 g (15 mol) of 96% sulfuric acid are carefully added. 367 g (3.0 mol) of benzoic acid are introduced into the sulfuric acid, which at this point has a temperature of about 100° C., over a period of about 10 minutes while stirring vigorously (during this the temperature drops to about 80° C.). The mixture is subsequently heated to an internal temperature of 100° C., the benzoic acid dissolving almost completely. 325 g (3.0 mol) of 1,2-phenylenediamine are subsequently metered in at such a rate that the temperature of the mixture does not rise above 125° C. After completion of the addition the mixture is heated to reflux temperature (about 178° C.) and stirred for a further 6 hours at this temperature, during which a small proportion of the benzoic acid sublimes. The mixture is then stirred into 6 l of water at a temperature of 100° C. and then stirred for a further 30 minutes at 100° C. and the precipitate is then filtered off with suction and washed with 2 l of water at a temperature of 80° C. until free of sulfate. The dried crude product (580 g, 70% of theory) is suspended in 2.5 l of water and the pH is adjusted to 8 with 32% sodium hydroxide solution. After addition of 20 g of activated carbon the mixture is stirred for a further 60 minutes at room temperature and subsequently clarified by filtration. The filtrate is heated to 80° C. and the pH is adjusted to 3 with concentrated sulfuric acid. The precipitated product is filtered off with suction while hot, washed with 4 l of water at a temperature of 90° C. and dried to constant weight in a vacuum drying cabinet at 75° C. and 20 mbar. 493 g (1.8 mol, 60% of theory) of 2-phenylbenzimidazole-5-sulfonic acid are thus obtained.

Example 6

A 2 l four-necked flask was initially charged with 1022 g (10 mol) of 96% sulfuric acid. 166.1 g (1 mol) of terephthalic acid are introduced into this over a period of about 10 minutes while stirring vigorously. A solution at a temperature of 80° C. and containing 216.6 g (2.0 mol) of 1,2-phenylenediamine in 140 ml of fully deionized water is metered into the sulfuric acid at such a rate that the temperature of the mixture does not rise above 130° C. After completion of the addition the mixture is heated to from 175° to 180° C. and stirred for about 4 hours at this temperature. During this time water is distilled off under reduced pressure. At the end of the reaction time the hot mixture is stirred into 4 l of water at a temperature of 80° C. The mixture is again allowed to cool to 80° C., the precipitate is filtered off with suction and washed with 2 l of water at a temperature of 80° C. The crude product is suspended in 2.5 l of water and the pH is adjusted to 8 with 32% sodium hydroxide solution. After addition of 20 g of activated carbon the mixture is stirred for a further 60 minutes at room temperature and subsequently clarified by filtration. The filtrate is first adjusted to a pH of 6.0 with concentrated sulfuric acid and then heated to 80° C. The pH is subsequently adjusted to 2.0 with concentrated sulfuric acid (temperature rise to about 100° C.). The mixture is again allowed to cool to 80° C., the precipitate is filtered off with suction and washed with 1 l of water at a temperature of 80°

C. (Test for freedom from sulfate). The final product is dried to constant weight in a vacuum drying cabinet at 75° C. and about 20 mbar. 306 g (65%) of 1,4-bis-(B-sulfobenzimidazol-2'-yl)benzene are thus obtained. The spectra of the new compounds are as expected ($\lambda_{max}$=349 nm).

The compounds below are prepared analogously:

From isophthalic acid:
1,3-bis-1(5-sulfobenzimidazol-2'-yl)benzene [sic] ($\lambda_{max}$= 307 nm).

From 1,3,5-benzenetricarboxylic acid:
1,3,5-tris(5-sulfobenzimidazol-2'-yl)benzene.

We claim:

1. A single-step process for preparing a 2-arylbenzimidazole-5-sulfonic acid of formula I

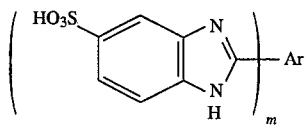
I wherein

Ar is phenyl or phenyl substituted by one or more $C_{1-6}$-alkyl or -alkoxy groups, and m is 1, 2 or 3, comprising reacting o-phenylenediamine in a solvent in the presence of sulfuric acid at between room temperature and 250° C.

with a benzoic acid derivative of formula II

Ar—(X)$_m$     II wherein

Ar is as defined above, and

X is COO-alkyl, wherein alkyl is $C_{1-6}$-n-alkyl, COOH, COCl, COBr or CN.

2. A process of claim 1, wherein the o-phenylenediame and the benzoic acid derivative of formula II are introduced together into the sulfuric acid.

3. A process of claim 1, wherein the sulfuric acid is the solvent for the reaction.

4. A process of claim 1, wherein the solvent comprises 1–50% water.

5. A process of claim 1, wherein the reaction is conducted for 1–5 hours at 80°–140° C., and then for an additional 0.5–5 hours at 170°–250° C.

6. A process of claim 1, wherein m is 1.

7. A process of claim 1, wherein m is 2 and

Ar is 1,3- or 1,4-phenylene or 1,3- or 1,4-phenylene substituted by 1-4 $C_{1-6}$-alkyl or -alkoxy groups.

8. A process of claim 1, wherein m is 3 and

Ar is

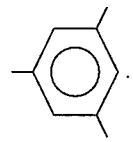

* * * * *